United States Patent
McVey et al.

(10) Patent No.: US 7,651,667 B2
(45) Date of Patent: Jan. 26, 2010

(54) ACTIVATED VAPOR TREATMENT FOR NEUTRALIZING WARFARE AGENTS

(75) Inventors: Iain F. McVey, Lakewood, OH (US); Lewis I. Schwartz, Shaker Heights, OH (US); Michael A. Centanni, Parma, OH (US); George W. Wagner, Elkton, MD (US)

(73) Assignees: The United States of America as represented by the Secretary of the Army, Washington, DC (US); Steris Inc., Temecula, CA (US)

( * ) Notice: Subject to any disclaimer, the term of this patent is extended or adjusted under 35 U.S.C. 154(b) by 316 days.

(21) Appl. No.: 11/401,733

(22) Filed: Apr. 10, 2006

(65) Prior Publication Data

US 2009/0311152 A1    Dec. 17, 2009

Related U.S. Application Data

(62) Division of application No. 10/422,472, filed on Apr. 24, 2003, now Pat. No. 7,102,052.

(51) Int. Cl.
*B01J 12/00* (2006.01)
*A61L 2/00* (2006.01)
*A61L 9/00* (2006.01)
*A61L 2/20* (2006.01)

(52) U.S. Cl. ............ 422/129; 422/28; 422/33; 422/292; 422/298; 422/306

(58) Field of Classification Search .............. 422/129, 422/28, 33, 292, 298, 306
See application file for complete search history.

(56) References Cited

U.S. PATENT DOCUMENTS

| | | | |
|---|---|---|---|
| 4,042,336 A * | 8/1977 | Larsson | 422/58 |
| 4,695,327 A | 9/1987 | Grebinski | |
| 4,867,799 A | 9/1989 | Grebinski | |
| 4,896,547 A | 1/1990 | Arney et al. | |
| 5,430,228 A | 7/1995 | Ciambrone et al. | |
| 5,667,753 A * | 9/1997 | Jacobs et al. | 422/29 |
| 5,714,128 A | 2/1998 | Ritter | |
| 5,779,973 A * | 7/1998 | Edwards et al. | 422/28 |
| 5,998,691 A | 12/1999 | Abel et al. | |
| 6,011,193 A | 1/2000 | Myler et al. | |

(Continued)

FOREIGN PATENT DOCUMENTS

| | | |
|---|---|---|
| DE | 300 472 A7 | 6/1992 |
| DE | 19732594 | 2/1999 |
| EP | 1 166 825 A1 | 1/2002 |
| FR | 2651133 | 3/1991 |
| FR | 2766724 | 2/1999 |
| JP | 2002066308 | 3/2002 |

OTHER PUBLICATIONS

Wagner, et al., "Rapid Nucleophilic/Oxidative Decontamination of Chemical Warfare Agents", Ind. Eng. Chem. Res. 2002, 41, 1925-1928.

*Primary Examiner*—Walter D Griffin
*Assistant Examiner*—Natasha Young
(74) *Attorney, Agent, or Firm*—Fay Sharpe LLP

(57) ABSTRACT

Hydrogen peroxide is vaporized (20) and mixed (30) with ammonia gas in a ratio between 1:1 and 1:0.0001. The peroxide and ammonia vapor mixture are conveyed to a treatment area (10) to neutralize V-type, H-type, or G-type chemical agents, pathogens, biotoxins, spores, prions, and the like. The ammonia provides the primary deactivating agent for G-type agents with the peroxide acting as an accelerator. The peroxide acts as the primary agent for deactivating V-type and H-type agents, pathogens, biotoxins, spores, and prions. The ammonia acts as an accelerator in at least some of these peroxide deactivation reactions.

6 Claims, 2 Drawing Sheets

U.S. PATENT DOCUMENTS

| | | |
|---|---|---|
| 6,080,906 A | 6/2000 | Johnson et al. |
| 6,096,283 A | 8/2000 | Cooper et al. |
| 6,121,506 A * | 9/2000 | Abel et al. .................. 588/318 |
| 6,132,628 A * | 10/2000 | Barak ......................... 210/756 |
| 6,245,957 B1 | 6/2001 | Wagner et al. .............. 588/200 |
| 6,375,697 B2 | 4/2002 | Davies |
| 6,566,574 B1 | 5/2003 | Tadros et al. |
| 6,790,249 B2 | 9/2004 | Davies |
| 6,855,328 B2 * | 2/2005 | Hei et al. .................... 424/405 |
| 7,102,052 B2 | 9/2006 | McVey et al. |
| 2001/0049926 A1 | 12/2001 | Davies |
| 2003/0035754 A1 | 2/2003 | Sias et al. |
| 2003/0045767 A1 | 3/2003 | Brown |
| 2003/0050525 A1 | 3/2003 | Ishiyama |
| 2004/0057868 A1 | 3/2004 | McVey et al. |
| 2006/0252974 A1 | 11/2006 | McVey et al. |

* cited by examiner

ACTIVATED VAPOR TREATMENT FOR NEUTRALIZING WARFARE AGENTS

This application is a divisional application of U.S. application Ser. No. 10/422,472, filed Apr. 24, 2003 now U.S. Pat. No. 7,102,052.

GOVERNMENT INTEREST

The invention described herein may be manufactured, licensed, and used by or for the U.S. government.

BACKGROUND OF THE INVENTION

The present application relates to the art of deactivating biological and chemical warfare agents. It finds particular application in conjunction with G-type agents. However, it will be appreciated that it also will find application in conjunction with V-type and H-type agents, as well as biological agents.

Liquid oxidants have been developed which can deactivate biological warfare agents. See, for example, U.S. Pat. No. 6,245,957 to Wagner, et al. In Wagner, a strong oxidant solution is sprayed as a liquid onto equipment in the field which is or has potentially been contaminated with biological or chemical warfare agents. After treatment, the solution is rinsed from the equipment with water which can be permitted to flow onto the ground as non-toxic. Although effective, the liquid Wagner solution has drawbacks. First, it is difficult for liquids to penetrate crevasses, fine cracks, ducts, and partially protected or lapping parts. Second, in enclosed spaces such as the interior of airplanes, tanks, and buildings, cleanup and disposal of the liquid solution can be problematic. Third, liquids can damage some equipment, such as electronic or electrical equipment.

Blistering agents, such as HD (sulphur mustard) undergo oxidation to non-vesicating products (sulphide to sulphoxide). With the correct choice of agents, the further oxidation to the sulphone does not occur. This is preferable as both the sulfide and the sulphone have vesicant properties; whereas, the sulphoxide is non-vesicant.

Peroxide causes a perhydrolysis reaction neutralizing V-type nerve agents, e.g., VX nerve agent. In the perhydrolysis reaction, the peroxide moiety substitutes one of the groups around the phosphorous atom at the active site of the nerve agent molecules. Perhydrolysis is more effective against V-type nerve agents than base catalyzed hydrolysis by water. In the presence of water, such as a water and ammonia wash, the base catalyzed hydrolysis reaction can form EA2192 which is also highly toxic.

On the other hand, G-agents, such as GD does not undergo an autocatalytic perhydrolysis neutralizing reaction with hydrogen peroxide. Rather, G-type agents are typically deactivated with an ammonia based compound.

The present application delivers a vapor phase deactivant which is effective against GV and H-type agents, as well as against biological agents.

SUMMARY OF THE INVENTION

In accordance with one aspect of the present invention, surfaces are treated with a blend of peroxy and ammonia vapor to deactivate biological and chemical warfare agent residues.

In accordance with another aspect of the present invention, the surfaces are treated with a combination of an oxidizing vapor and a basic vapor, or mist, preferably ammonia or a short chain alkyl amine.

One advantage of the present invention resides in its effectiveness against a wide variety of chemical warfare agents including both V and G-type agents.

Another advantage of the present invention resides in its effectiveness against biological agents.

Another advantage of the present invention resides in its ease of cleanup.

Yet another advantage of the present invention resides in compatibility with electrical equipment.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
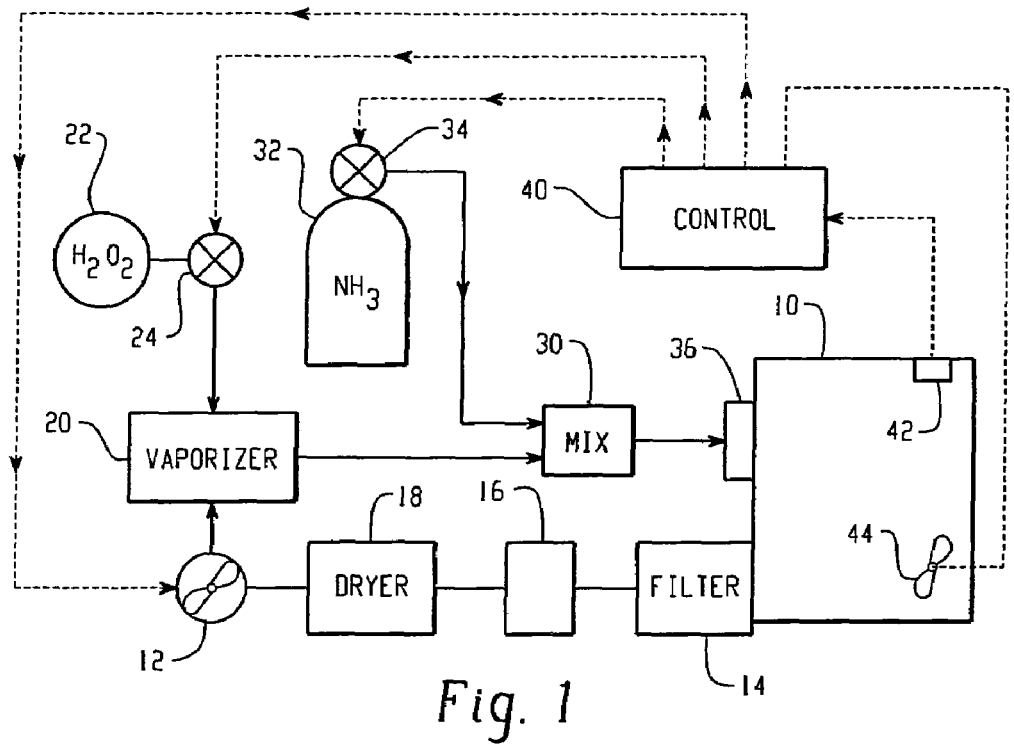
FIG. 1 is a diagrammatic illustration of a vapor treatment system in accordance with the present invention.

With reference to FIG. 1, a treatment enclosure 10 receives or is itself a part of a structure potentially contaminated with biological or chemical warfare agents. Typically biologically active substances include pathogens, biotoxins, prions, spores, and the like. Typical chemical agents include H-type blistering agents such as mustard gas, and V-type and G-type nerve agents. The treatment enclosure 10, in one embodiment, is a dedicated chamber that is adapted to receive items to be generated and then sealed. The chamber can be a fixed structure, a tent that is mounted around the object to be treated, or the like. In another embodiment, the enclosure includes the interior of a warehouse, room, aircraft, tank, or other vehicle whose interior surfaces or items contained therein are to be treated.

A fan or blower 12 draws environmental gas, typically air, from the enclosure 10 through a biological or chemical hazard filter 14. A catalytic destroyer 16 breaks down hydrogen peroxide into water vapor. A dryer 18 removes the water vapor from the recirculated gas to control the humidity of the carrier gas.

The filtered and dried air is supplied to a vaporizer 20 which vaporizes a liquid oxidant, preferably hydrogen peroxide, from a liquid hydrogen peroxide source 22. Other strong oxidants such as hypochlorites, ozone solutions, peracetic acid, and the like are also contemplated. Optionally, a cosolvent, such as alcohol, is mixed with the oxidant liquid. A valve 24 or other appropriate control means controls a rate at which the liquid hydrogen peroxide is vaporized.

The hydrogen peroxide vapor is fed to a mixing chamber or region 30 where the hydrogen peroxide vapor and air mixture is mixed with a basic gas or mist, preferably ammonia gas. However, short chain alkyl amines are also contemplated. Ammonia gas is supplied from a source or reservoir 32 such as a high pressure tank holding compressed ammonia gas. A control or regulator valve 34 controls the amount of ammonia vapor supplied to the mixing region 30. The mixture of ammonia and hydrogen peroxide vapor is immediately and continuously supplied to the treatment chamber 10. Preferably, a biological or chemical contaminant filter 36 is mounted at an inlet to the chamber.

A controller 40 includes one or more monitors 42 disposed in the treatment chamber 10 to monitor ambient conditions. Based on the monitored ambient conditions, the controller controls one or more of the control valves 24, 34 to control the relative concentrations of hydrogen peroxide and ammonia vapor, the blower 12 to control the amount of air flow, fans 44 in the chamber for distributing the treatment gas around the chamber, and the like. Preferably, the controller 40 controls the valves 24, 34 such that a mixture of peroxide vapor and ammonia in the mixing region 30 occurs which achieves an ammonia concentration with a range of 1 to 0.0001 times the nominal peroxy vapor concentration.

In the embodiment of FIG. 1, a closed-loop system is illustrated in which the same carrier gas is recirculated and used over. Alternately, an open-loop system can be utilized, in which fresh atmospheric air is supplied to the vaporizer, preferably filtered and dried, and air exiting the chamber is filtered to prevent the biological or chemical contaminants from escaping and discharging to the atmosphere.

Hydrogen peroxide vapor alone is effective against blistering agents, HD, and nerve agents, such as VX, which exhibit selective oxidation and selective perhydrolysis. By the addition of ammonia to the vapor stream, the hydrolysis-based deactivation of GD is also effected.

Under exposure to hydrogen peroxide vapor, HD is selectively oxidized to a non-vesicant sulphoxide. This reaction with the vaporized hydrogen peroxide occurs rapidly, more rapidly with vapor than with liquid hydrogen peroxide solutions. A mass transfer of hydrogen peroxide between the vapor and the liquid agent results in an accumulation of hydrogen peroxide in the liquid phase which causes oxidation to occur rapidly. The excess of dissolved oxidant assures completion of the oxidation process. In liquid neutral peroxide solutions, VX undergoes partial autocatalytic perhydrolysis owing to the basicity of its amine group. However, this process may not lead to total destruction. In the presence of activators which buffer the peroxide to basic pHs, the perhydrolysis proceeds to complete destruction.

When exposed to hydrogen peroxide vapor, VX undergoes similar perhydrolysis with the basicity of the amine group of the VX molecule effecting autocatalytic perhydrolysis. Hydrogen peroxide is constantly replenished by mass transfer between the liquid agent and the vapor flowing over it maintaining an adequate supply of the peroxy anion for the reaction. The acidic products that are produced by the perhydrolysis are volatile, and are carried away with the flowing vapor. Unlike the stagnant liquids, this removal of the acidic products prevents them from accumulating and lowering the pH to the point that the reaction stops. Having catalytic amounts of ammonia in the vapor product has no adverse effect on the neutralization of VX.

The GD does not undergo autocatalytic perhydrolysis with either liquid or vaporized hydrogen peroxide alone. However, the GD is susceptible to deactivation by base catalyzed hydrolysis and perhydrolysis. In solution, perhydrolysis is about four times as fast as base catalyzed hydrolysis. Both hydrolysis and perhydrolysis result in the formation of the same non-toxic inactivation products. GD exposed to hydrogen peroxide and ammonia or other short chain alkyl amines which raise the pH undergoes rapid perhydrolysis and/or hydrolysis, as long as the pH remains elevated. Exposure to hydrogen peroxide vapor alone does not cause the perhydrolysis to occur. However, when the ammonia is added to the hydrogen peroxide vapor, hydrolysis to form the non-toxic inactivation products occur. The hydrolysis reaction results from the basicity of the ammonia and the presence of water that is absorbed in the hygroscopic GD liquid.

Figure 2:
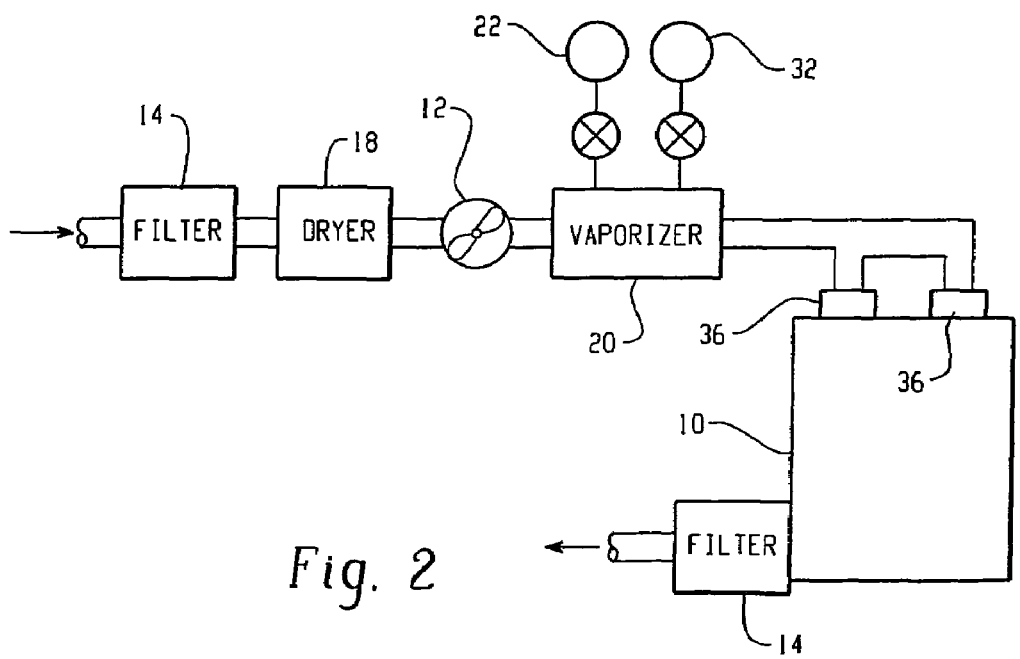
FIG. 2 is an alternate embodiment of the treatment system of FIG. 1.

With reference to FIG. 2, an open-loop system is illustrated. The blower 12 pulls air through a filter 14 and, optionally a dehumidifier, before pushing it through the vaporizer 20. A peroxy vapor source 22 and a short chain alkyl amine source 34 provide liquid peroxy and alkyl amines to the vaporizer. Alternately, separate vaporizers may be provided for each. The peroxy and alkyl amine vapors can be injected separately into the carrier gas in a mixing region. As yet another alternative, the alkyl amines and the peroxy liquids can be supplied to the vaporizer alternately. The output of the vaporizer is connected to an interior region with surfaces to be decontaminated.

Figure 3:
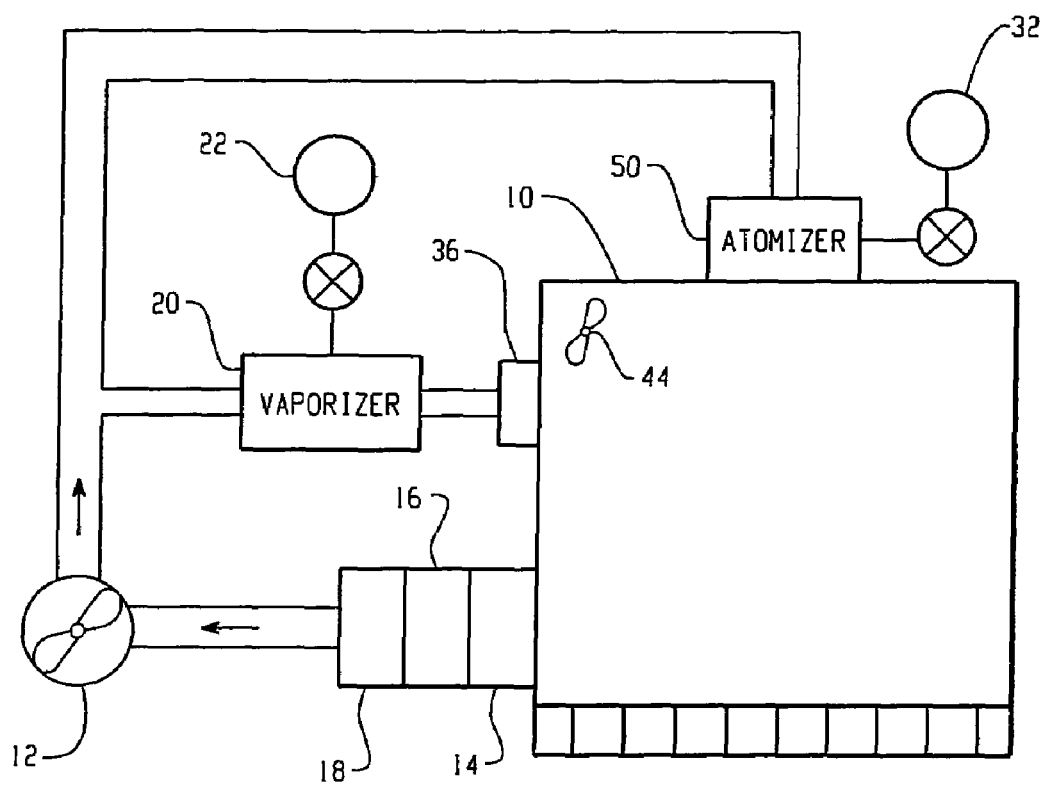
FIG. 3 is another alternate embodiment of the vapor treatment system.

With reference to FIG. 3, the carrier gas is filtered 14, peroxide destroyed 16, and dried 18. The blower 12 blows the dry gas to the vaporizer 20 which vaporizes liquid peroxy from the source 22. The liquid peroxy vapor is supplied directly to the treatment region 10. An atomizer 50 receives a liquid alkaline solution from a reservoir 52 which it atomizes or mists into mist that is discharged into the chamber 10. A portion of the carrier gas optionally flows through the mister to entrain and carry the mist throughout the chamber. Alternately, the alkaline solution can be vaporized. Suitable alkaline solutions include water-based solutions of potassium and other carbonates, molybdates, ammonium salts, and the like.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for deactivating biologically active substances comprising:
   a means for subjecting the biologically active substances to a mixture of a strong oxidant compound and an alkaline compound, both in a gaseous form, the subjecting means including:
      a vaporizer for vaporizing a peroxy liquid;
      a supply of ammonia or a short-chain alkyl amine gas; and
      a mixing region for mixing the gas and vapor.

2. An apparatus for deactivating biologically active substances comprising:
   a means for subjecting the biologically active substances to a mixture of a strong oxidant compound and an alkaline compound, both in a gaseous form, the subjecting means including:
      a vaporizer for vaporizing a liquid hydrogen peroxide;
      a liquid hydrogen peroxide source for supplying liquid hydrogen peroxide to the vaporizer, and
      a supply of ammonia or a short-chain alkyl amine gas, the supply of ammonia or alkyl amine gas including a compressed ammonia gas tank.

3. The apparatus as set forth in claim 2 further including:
   a control means which controls a rate of supplying the hydrogen peroxide to the vaporizer and a rate of supplying the ammonia gas to achieve a peroxide vapor to ammonia vapor ratio between 1:1 and 1:0.0001.

4. The apparatus as set forth in claim 3 further including:
a chamber connected with the mixing region for receiving items contaminated with the biologically active substance.

5. An apparatus for deactivating biologically active substances comprising:
a chamber;
a means for subjecting the biologically active substances to a mixture of a strong oxidant compound and an alkaline compound, both in a gaseous form, the subjecting means including:
a means for vaporizing a peroxy liquid to form the gaseous strong oxidant compound, fluidly connected with the chamber; and,
a separate means for atomizing or vaporizing an alkaline liquid to form the gaseous alkaline compound, fluidly connected with the chamber.

6. The apparatus as set forth in claim 1, further including:
a chamber connected with the peroxy vaporizing means and the atomizing or vaporizing means for receiving the vapor or mist.

* * * * *